US 6,632,228 B2

(12) United States Patent
Fortier et al.

(10) Patent No.: US 6,632,228 B2
(45) Date of Patent: Oct. 14, 2003

(54) SYSTEM, METHOD, AND APPARATUS FOR ACCURATELY DEPLOYING PARTICULAR MEDICAL APPLIANCES AT A TARGET SITE

(75) Inventors: Richard Fortier, Concord, MA (US); Mark Bowen, Stow, MA (US); Margaret McCabe, Fremont, CA (US)

(73) Assignee: SciMed Life System, Inc., Maple Grove, MN (US)

( * ) Notice: Subject to any disclaimer, the term of this patent is extended or adjusted under 35 U.S.C. 154(b) by 0 days.

(21) Appl. No.: 09/902,636

(22) Filed: Jul. 12, 2001

(65) Prior Publication Data

US 2002/0026199 A1 Feb. 28, 2002

Related U.S. Application Data

(60) Provisional application No. 60/226,901, filed on Aug. 23, 2000.

(51) Int. Cl.[7] .............................................. A61B 17/10
(52) U.S. Cl. ..................................................... 606/140
(58) Field of Search .................................. 606/108, 139, 606/140, 141, 144, 148; 221/36, 40, 312 C

(56) References Cited

U.S. PATENT DOCUMENTS

| 5,398,844 A | | 3/1995 | Zaslavsky et al. |
| 5,766,216 A | * | 6/1998 | Gangal et al. ............... 606/140 |
| 5,817,033 A | | 10/1998 | DeSantis et al. |
| 5,857,585 A | | 1/1999 | Tolkoff et al. |
| 6,280,452 B1 | * | 8/2001 | Mears ........................ 606/140 |

* cited by examiner

Primary Examiner—Eduardo C. Robert
(74) Attorney, Agent, or Firm—Kenyon & Kenyon

(57) ABSTRACT

The present invention regards system, method, and apparatus for selectively and accurately deploying one or more sequentially positioned medical appliances from a portable medical device. An apparatus, in accord with one embodiment of the present invention, includes a ligation tip having an internal passage and an outside surface wherein the outside surface has a plurality of sequentially ordered deployable medical appliances in contact with it. The apparatus also includes a body having a channel in communication with the internal passage of the ligation tip, a string passing through the internal passage and the channel, and an indicator, coupled to the string, for affirmatively verifying that a specific medical appliance, from the plurality of sequentially ordered medical appliances, has been deployed from the ligation tip.

16 Claims, 5 Drawing Sheets

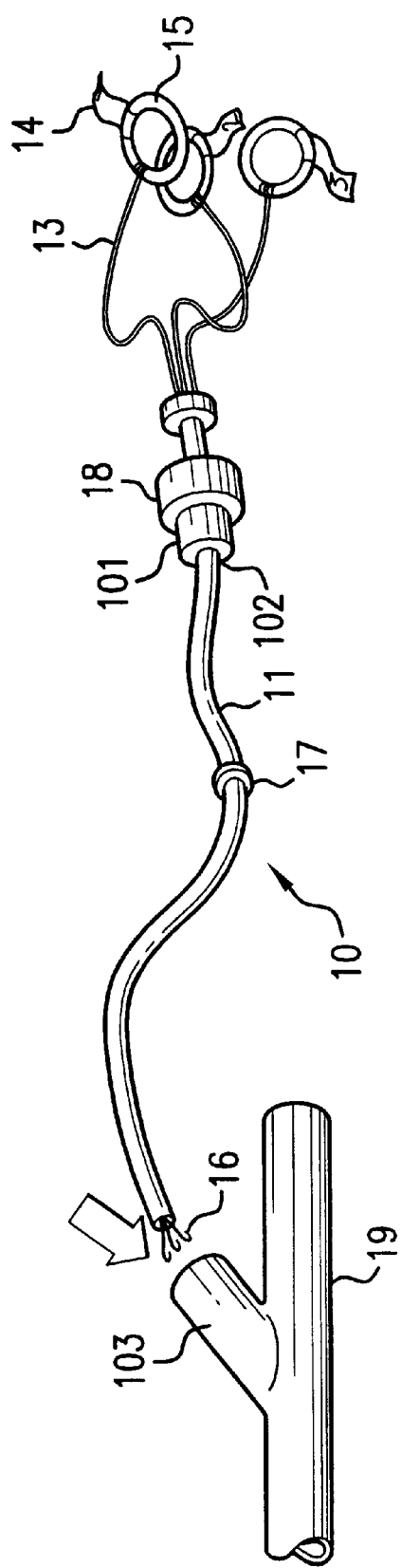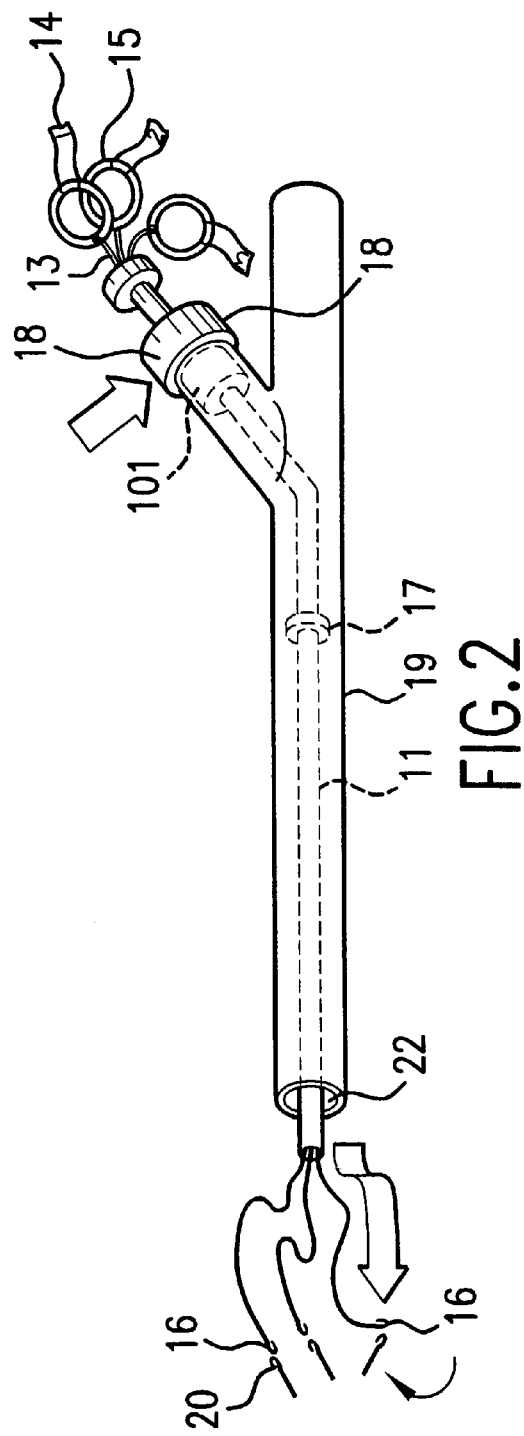

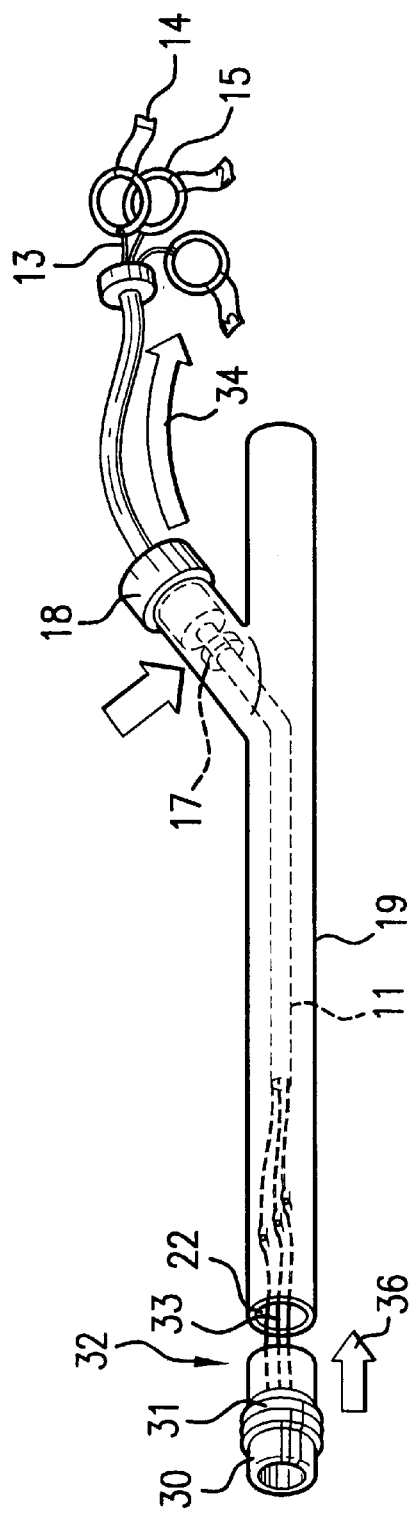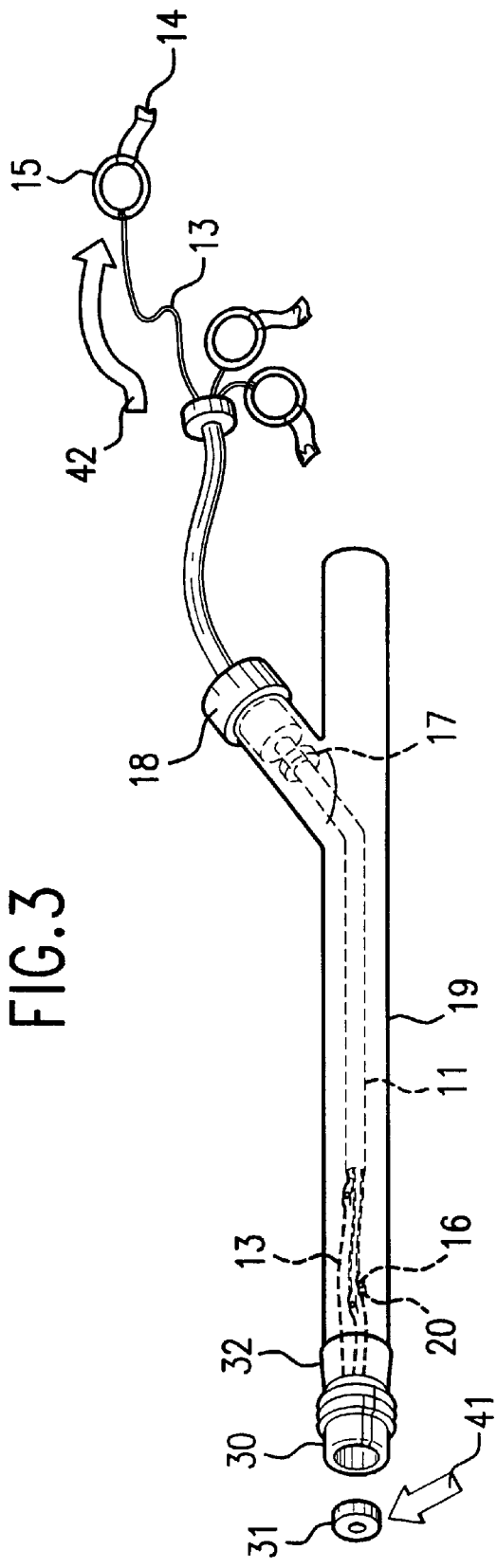

SYSTEM, METHOD, AND APPARATUS FOR ACCURATELY DEPLOYING PARTICULAR MEDICAL APPLIANCES AT A TARGET SITE

RELATED APPLICATIONS

This application claims the benefit of U.S. Provisional Application Ser. No. 60/226,901, filed Aug. 23, 2000, and incorporates that application herein, in its entirety, by reference.

FIELD OF THE INVENTION

The present invention generally relates to method and apparatus for the performance of medical procedures at a target site remote from the medical practitioner performing the procedure. More particularly the present invention relates to method and apparatus for accurately deploying particular medical appliances from a medical device after the medical device has been positioned at a site targeted to receive the medical appliance.

BACKGROUND INFORMATION

Medical procedures may be performed by a practitioner through direct contact and interface with a target site as well as through remote access to the target site via medical devices, such as endoscopes, which are designed to extend the practitioner's reach. By extending the practitioner's reach these devices allow some medical procedures, previously performed only through invasive procedures, to be performed through non-invasive methodologies. One drawback of these extension devices and remote access methodologies is that a practitioner may not be able to watch the procedure being performed and, thus, may not be able to visually determine if the procedure he is performing has been properly completed.

For instance, when an endoscope is being used for the ligation of a polyp deep within a patient's body, the distal end of the endoscope, where the procedure is actually carried out, is not directly visible to the practitioner. Nevertheless, despite this handicap, the practitioner must first maneuver the distal end of the endoscope to the targeted polyp and then, in less sophisticated systems, must perform the procedure relying solely on his or her own tactile abilities. In one endoscopic ligation unit this process would involve pulling on a single string emerging from the proximal end of the endoscope until one of the several bands, around which the string was wrapped at its distal end, was deployed. In this unit, if the string is pulled too far, more than one band may be deployed and, if the string is not pulled far enough, a band may not be deployed at all. During its use, once the practitioner thought that a single band was deployed, but without positive confirmation, the practitioner would relocate the distal end of the endoscope to deploy another band or if the procedure was completed, retract the endoscope from the patient.

If the ligation bands had become entangled during the procedure they could remain on the distal end of the ligation unit and provide notice to the practitioner, upon the endoscope's removal, that the procedure was not properly performed. Conversely, if too many bands were deployed during the procedure or if they were deployed in the wrong areas, it would be difficult if not impossible for the practitioner to immediately discern, based on viewing the distal end of the ligation unit, that the bands had been improperly deployed from the endoscope.

SUMMARY OF THE INVENTION

The present invention regards system, method, and apparatus for selectively and accurately deploying one or more sequentially positioned medical appliances from a portable medical device. An apparatus, in accord with one embodiment of the present invention, includes a ligation tip having an internal passage and an outside surface wherein the outside surface has a plurality of sequentially ordered deployable medical appliances in contact with it. The apparatus in this embodiment also includes a body having a channel in communication with the internal passage of the ligation tip, a string passing through the internal passage and the channel, and a means, coupled to the string, for affirmatively verifying that a specific medical appliance, from the plurality of sequentially ordered medical appliances, has been deployed from the ligation tip.

A system for selectively deploying one or more sequentially positioned medical appliances from a portable medical device to a target site is provided in an alternative embodiment of the present invention. This system may include a flexible sheath having a channel, an inside surface, an outside surface, a distal end, and a proximal end. In addition, this sheath may contain a plurality of strings positioned within its channel wherein each string may have a first end and a second end, wherein the first end of at least one string may be coupled to a pull that has a unique marking, and wherein the second end of the string that is coupled to the unique marking may be in physical communication with a catch. The system in this embodiment may also include an external sealing plug positioned along the outside surface of the sheath between the sheath's distal end and proximal end, wherein the plug has a passage sized to slidably couple the sheath to it.

BRIEF DESCRIPTION OF THE DRAWINGS

FIG. 1 is a side perspective view of a removeable string system containing a plurality of strings prior to its insertion into a body in accord with one embodiment of the present invention.

FIG. 2 is a side perspective view of the removeable string system containing a plurality of strings from FIG. 1 after it has been inserted into the body in accord with one embodiment of the present invention.

FIG. 3 is a side perspective view of the removeable string system containing a plurality of strings from FIG. 1 after it has been inserted into the body and after the strings have been connected to the filaments of the ligation tip in accord with one embodiment of the present invention.

FIG. 4 is a side perspective view of one of the strings, from the plurality of strings, being pulled in order to deploy a ligation band in accord with one embodiment of the present invention.

DETAILED DESCRIPTION

Figure 5:
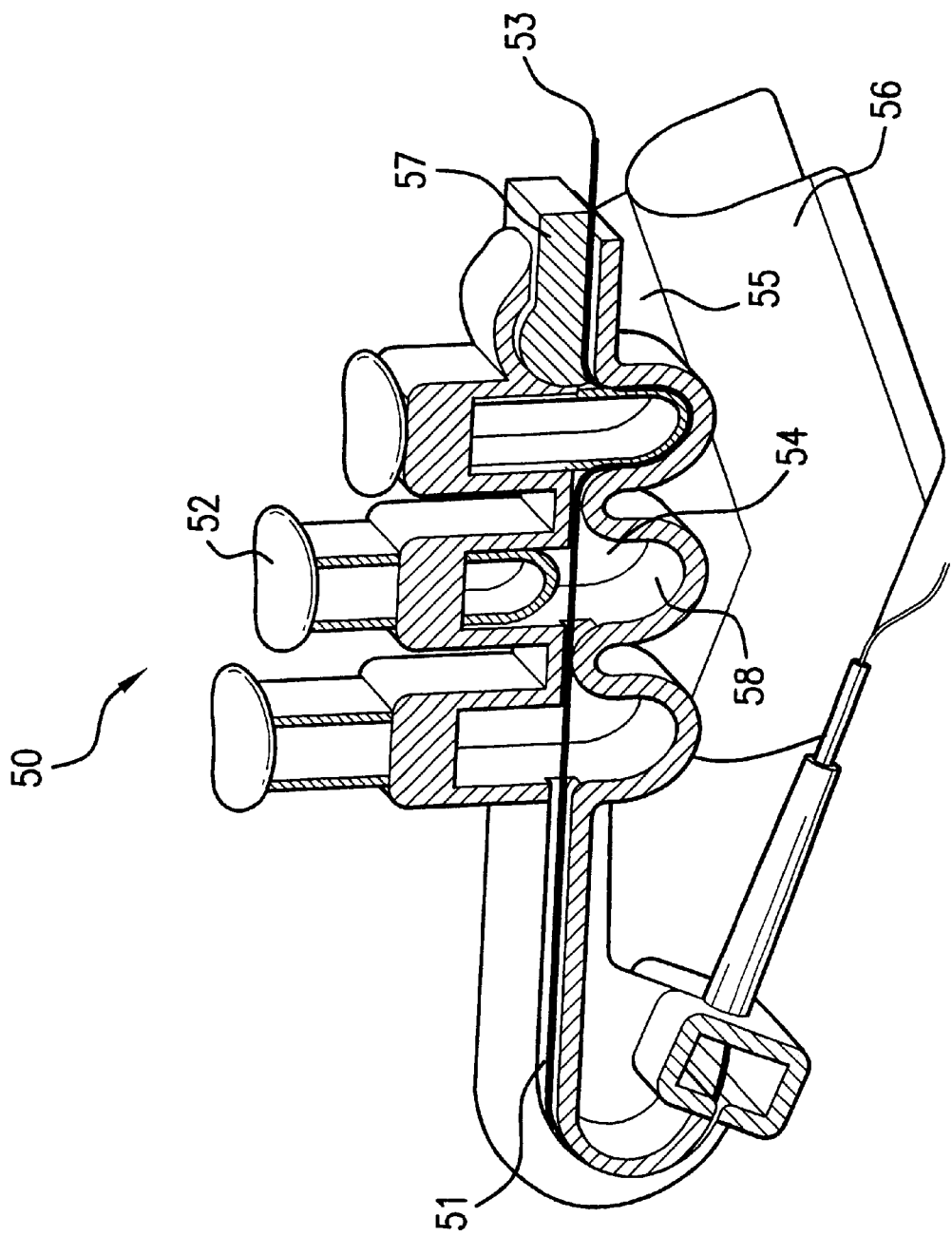
FIG. 5 is a side perspective view of a medical apparatus in accord with one embodiment of the present invention.

FIGS. 1–4 illustrate the components, assembly, and use of a medical device or apparatus that may be used to deploy ligation bands or other medical appliances within the body of a patient in accord with one embodiment of the present invention. The medical device depicted in these figures may be used independently or in conjunction with an endoscope or other device to perform endoscopic tubal ligations as well as numerous other procedures.

FIG. 1 is a side perspective view of some of the components of the medical device that is depicted in FIGS. 1–4 (wherein like elements have been numbered throughout with like numerals). FIG. 1 illustrates the removable cable system 10 prior to its insertion into the y-extension extension 103 of tube or body 19 which may be an endoscope or any other device capable of creating an operating channel to a target site in the patient in accord with one embodiment of the present invention. As can be seen, this removable cable system 10 contains a plurality of filaments or strings 13 running through a flexible sheath 11. The sheath 11, which may be made from rubber, plastic or any other flexible and resilient material, may have a circular, hexagonal, octangular or other cross-sectional shape. However, regardless of which cross-sectional shape is used, it is preferable that the cross-sectional area be sized such that the sheath 11 may readily encase each of the strings 13 traveling through it, that the strings may not be bound within the sheath 11, that the strings 13 may be readily pulled back and forth through the sheath 11 and that the sheath 11 containing the strings 13 may be sized to fit within the body 19 and the y-extension extension 103 of the body 19.

The system 10 of FIG. 1 may also include a sealing plug 18 having a bore 102 traveling through it wherein the bore 102 is sized to allow the sheath 11 to slide back and forth within it. This sealing plug 18 may be made from the same material as the sheath 11 or it may be made from a separate material. It may also be manufactured in conjunction with the sheath 11 or it may be placed around the sheath 11 after the sheath 11 has been manufactured. Moreover it may be added to the sheath either before and after the strings have been placed within the sheath 11. The external sealing plug 18 may have a tang portion 101, as illustrated in FIG. 1, that is sized to frictionally secure the sealing plug 18 to the y-extension 103 of the body 19. When the tang portion 101 is inserted into the y-extension 103 the system 10 may continue to be able to slide in and out of the body 19 due to the size of the bore 102 in relation to the sheath 11. In an alternative configuration, rather than using friction to secure the tang 101 to the y-extension 103 the tang portion 101 may contain threads that may be used to secure the sealing plug 18 to the body 19. Moreover, in addition to this alternative configuration other securement configurations and methodologies, such as bendable clips and adhesives, may also be used to secure the sealing plug 18 to the y-extension 103 of the body 19.

The sheath 11 may also have a stopper 17 positioned on its outside surface. This stopper 17 may be made in conjunction with the sheath 11 or may be added at a later time. This stopper 17 is preferably fixedly secured to the sheath 11 and sized to prevent the sheath 11 from being completely slid through the bore 102 of the sealing plug 18.

The strings 13, which are located within the sheath 11, may have pulls 15 attached to one of their ends. These pulls 15 may have unique identifiers or tags 14 attached to them which act, with the pulls 15, as a means for affirmatively verifying that the specific medical appliance from a plurality of medical appliances, has been deployed. Alternatively, rather than using a pull and tag system the pulls 15 may, themselves, be colored or otherwise identified to allow them to be effectively distinguished from one another.

The opposite end of the strings 13, (i.e. those not coupled to the pulls 15) may terminate in a loop or catch 16 or may at least be in physical communication with the loop or catch 16. This catch 16 may be used, as shown in FIG. 3, to releasably connect the individual strings 13 of the system 10 to hooks 20 associated with individual ligating bands that surround the ligation tip 30 in FIG. 3 and may be deployed by pulling on the pulls 15 during a medical procedure.

As can be seen in FIG. 2 the removeable cable system 10 may be inserted into the y-extension extension 103 of the body 19 until the tang 101 of the sealing plug 18 comes to rest within the end of the y-extension 103. As can also be seen in this figure the sheath 11 and the strings 13 are sized such that when the sealing plug 18 comes to rest against the y-extension 103 of the body 19 the catches 16 extend past the distal end 22 of the body 19. By sizing the sheath 11 and strings 13, so that they are longer than this portion of the body 19, the catches 16 may be readily attached to hooks 20 of the ligation tip 30 shown in FIG. 3.

FIG. 3 illustrates a side view of the medical device from FIGS. 1–4 after the individual filaments 33 of the ligation tip 30 have been coupled to the strings 13 of the cable system 10. As indicated by arrow 36, once the requisite connections have been made between the filaments 33 and the strings 13, the end 32 of the ligation tip 30 may be slid around or into the open end 22 of the body 19. At the same time, to prevent the strings 13 and the filaments 33 from becoming entangled, the cable system 10 may be pulled, as indicated by arrow 34, to remove any slack in the lines created by the insertion and coupling process. As can be seen, the stopper 17 may act to limit the distance that the cable system 10 may be pulled through the sealing plug 18, and, thereby, prevent the premature deployment of all of the ligating bands from the tip 30 as would occur if the removable cable system 10 was pulled too far back up through the sealing plug 18.

Figure 6:
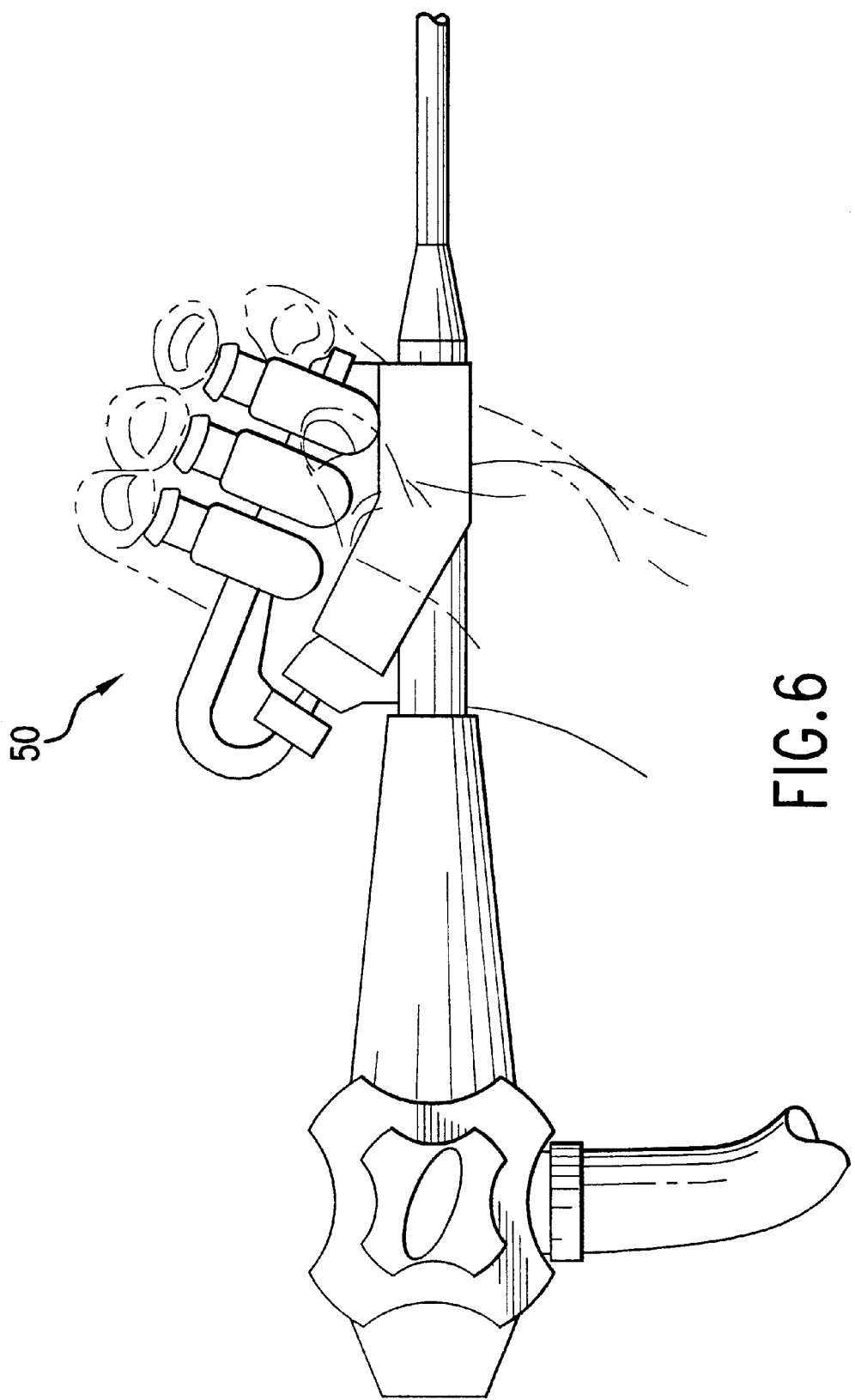
FIG. 6 is a side perspective view of the medical apparatus from FIG. 5 being used by a practitioner in accord with one embodiment of the present invention.

The ligation tip 30, which is fully evident in FIG. 4, may contain a plurality of ligation bands 31 that may be located around its outside surface. These ligation bands 31 may be individually coupled to the individual filaments 33 which are in turn individually coupled to the strings 13. Thus, in use, as depicted in FIG. 4, by pulling on one of the pulls 15 as indicated by arrow 42 a specific ligation band 31 may be deployed from the ligation tip 30 as indicated by arrow 41. Because each pull 15 has a unique marking to associate it with a specific deployable medical appliance, when an operator pulls a specifically marked pull, the operator will know which medical appliance, in this case a ligation band, is being deployed at that time. Thus, through this system, a practitioner may more accurately control the deployment of ligation bands from the distal end of a ligation unit as he can positively determine, from the proximal end of the device, which ligation band is being deployed FIG. 5 is a side perspective view of an alternative embodiment of the present invention. In FIG. 5 a means 50 for affirmatively verifying the deployment of a medical appliance from a plurality of medical appliances can be seen. Means 50 may be attached to an endoscope as illustrated in FIG. 6. Means 50 may contain a plunger 52, a body 56, a string 53, and a variable length string passageway 51 and may be used to deploy ligation bands or other medical appliances located at the distal end of an endoscope. Means 50 accomplishes this task by shortening or otherwise pulling on a string contained within the passageway 51 that is coupled to a plurality of deployable medical appliances at the distal end of the endoscope. This string is pulled or shortened by a specific predetermined distance by depressing one of the plungers 52 of the means 50. As the plunger 52 is depressed, the string 53 resident in the passageway 51 and coupled to anchoring point 57 will have its effective length shortened by the distance that it must now travel around the depressed plunger 52. Thus, by depressing the plunger 52, the string will be shortened and a ligation band or other device coupled to the string may be deployed by the medical device.

A specific method of using the means 50 from FIG. 5 may include coupling the body 56 to an endoscope and then threading a string 53 through the string passageway 51 and anchoring point 57. The distal end of the string 53 may then be threaded around each deployable medical appliance in sequential order. Then, as mentioned above, in order to deploy the medical appliance, the plunger 52 may be depressed, in order to draw the string 53 into the valley 58 associated with the plunger 53 thus altering the string's pathway and shortening its effective length. Consequently, when a plunger 52 is depressed, a medical appliance coupled to the string's distal end may be deployed from the distal end of the medical device. If a second medical appliance is to be deployed, a second plunger may be depressed while the first plunger is also depressed. Here, the effective length of the string will be twice shortened and the second medical appliance may be deployed. Likewise a third appliance may also be deployed by depressing the third plunger 52 while the first two are also depressed. The plungers in this embodiment may be depressed in any order to deploy the first, second, and the third medical appliances since the string is not bound underneath the depressed plungers but, is rather, able to slide back and forth underneath the depressed plunger.

Advantages of this configuration include that the operator can readily detect the number of medical appliances that have been deployed and that, as can be seen in FIG. 6, the user may use a single hand to hold the endoscope and to deploy the medical appliances. In an alternative embodiment the plungers may be retained by some locking mechanism after the plunger has been depressed into the valleys 58 so that it is not necessary to hold down the plungers in order to deploy several bands. Conversely, the plungers may be biased in an open position to reduce the likelihood that the plunger will be errantly depressed by a practitioner during a procedure.

Figure 7:
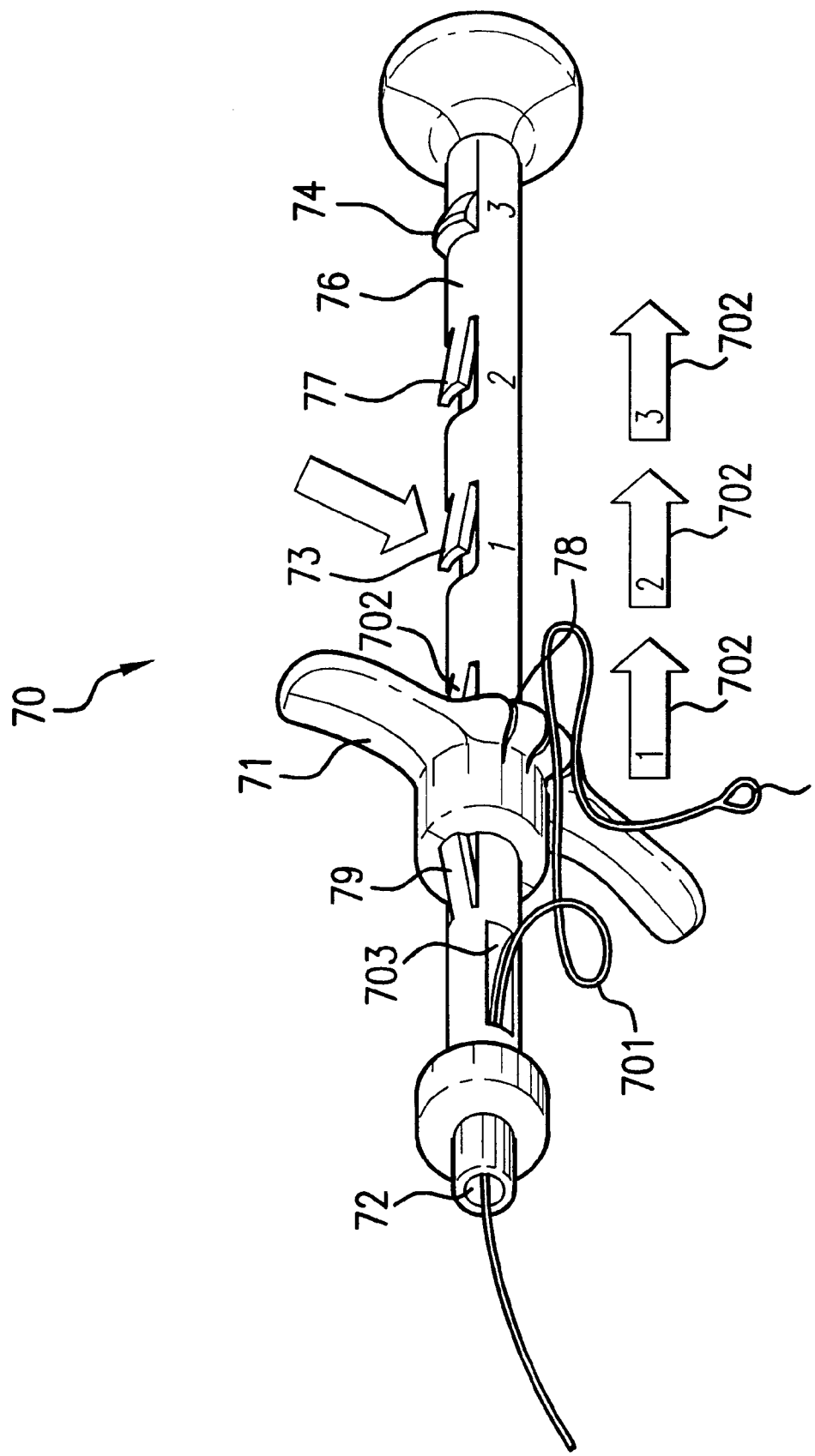
FIG. 7 is a side perspective view of a medical apparatus in accord with one embodiment of the present invention.

An alternative embodiment of a means 70 for affirmatively verifying the deployment of a specific medical appliance from a plurality of appliances is illustrated in FIG. 7. Means 70 may be placed at the distal end of an endoscope and may be used to pull a string a predetermined distance in order to deploy a ligation band in communication with the string from a ligation tip at the distal end of the endoscope. Means 70 may include a shaft 76, an opening 72, and a slidable handle 71 coupled to the shaft 76 and adapted to be slid over the shaft 76. The handle 71 may also contain several slots 78 that may be sized to secure a looped end 75 of a string 701 that may be attached to a plurality of ligation bands at the distal end of the endoscope or other device. Consequently, as the handle 71 is incrementally advanced down the shaft 76 the string 701 may be pulled by that same incremental distance as the handle 71 is slid.

Alternatively, in another embodiment, rather than having the string directly coupled to the ligating bands, a pulley system may be employed that adjusts or modifies the distance that handle 71 needs to be pulled before each ligation band is deployed. This pulley system or mechanical advantage system may increase the distance that the handle needs to be pulled or conversely decrease the distance that the handle needs to be pulled.

Also evident in FIG. 7 are a plurality of stops 73, 74, and 77 that protrude from the shaft 76 and may be sized to arrest the travel of the handle 71 as it slides down the body 76.

These stops may be integrally formed with the shaft 76 and may be compressible or incompressible. The compressible stops 73 and 77 in this embodiment may be designed so that they may be depressed to allow the handle 71 to be slid over them and down the shaft from position to position as indicated by arrows 702 in FIG. 7. Conversely, stop 74, which is fixed and incompressible in this embodiment, may act to prevent the handle 71 from sliding further down the body 76, thus acting as a block at the end of the handle 71. In addition, stops may also be used to arrest the travel of the handle 71 in the direction opposite to the arrows 702. An example of this type of stop is stop 79 which is shown preventing the handle 71 from sliding closer to opening 703 and obstructing the string 701 that protrudes from it. In this embodiment, as well as the embodiments discussed above, the shaft or body of the device may be made from rigid plastic, surgical grade metals, and other suitable materials.

System, method, and apparatus for deploying medical device from a medical appliance is provided. While several embodiments of the present invention have been described above other embodiments within the spirit and scope of the present invention are also possible.

What is claimed is:

1. A system for selectively deploying one or more sequentially positioned medical appliances from a portable medical device, having a passage through it, to a target site comprising:
   a flexible sheath having a channel, an inside surface, an outside surface, a distal end, and a proximal end;
   an external sealing plug positioned along the outside surface of the sheath between the distal end and the proximal end, the external sealing plug having a passage sized to slidably couple the sheath to the external sealing plug; and
   a plurality of strings positioned within the channel of the flexible sheath,
      wherein each string of the plurality of strings has a first end and a second end,
      the first end of at least one string coupled to a pull, the pull having a unique marking to distinguish it,
      the second end of the at least one string in physical communication with a catch.

2. The system of claim 1 further comprising:
   a stopper fixedly positioned on the outside surface of the sheath; and
   a ligation tip containing a plurality of deployable sequentially positioned medical appliances and at least one deployment string, the deployment string coupled to the catch and at least one of the medical appliances.

3. The system of claim 2 wherein the unique marking is a label identifying a specific medical appliance.

4. The system of claim 3 wherein the label contains a specific number or color.

5. The system of claim 2 wherein the stopper is sized to prohibit it from being pulled through the passage of the sealing plug.

6. The system of claim 1 wherein the sealing plug contains threads sized to rotatably connect it to the medical device.

7. The system of claim 1 wherein the sheath is polygonal and wherein the shape of the pull is associated with a medical appliance.

8. The system of claim 1 wherein the sealing plug is compressible and is sized to compressibly secure itself to an orifice of the medical device.

9. The system of claim 1 wherein the external sealing plug contains external threads sized to rotatably secure the plug to the medical device and wherein the medical device is an endoscope.

10. The system of claim 1 wherein the catch is a loop.

11. A method for selectively deploying one or more sequentially positioned medical appliances from a portable medical device to a target site comprising:
   inserting into an entrance of a portable medical device a removable cable system containing a plurality of strings, at least one string having a first end and a second end, the first end coupled to a pull, the pull marked to associate it with a specific deployable medical appliance, the second end ending in a catch, the catch associated with the specific deployable medical appliance, the plurality of strings encased within a sheath;
   advancing the removable cable system along the longitudinal axis of the portable medical device;
   exposing a second end of at least one string of the removable cable system from an orifice of the portable medical device;
   connecting the second end of the at least one string to a second string, the second string coupled to a deployable medical appliance, the deployable medical appliance positioned on a tip having a connecting end adapted to secure itself to the portable medical device; and
   installing the tip on the portable medical device.

12. The method of claim 11 further comprising:
   positioning the distal end of the medical device at a target site; and
   pulling at least one pull to deploy a medical appliance at the target site.

13. An apparatus for selectively deploying one or more sequentially positioned medical appliances from a portable medical device to a target site, the apparatus comprising:
   a ligation tip having a plurality of sequentially ordered deployable medical appliances in contact with its outside surface,
      the ligation tip having an internal passage;
   a body having a channel, the channel in communication with the internal passage of the ligation tip;
   at least one string passing through the internal passage and the channel, the at least one string being associated with at least one of the medical appliances from the plurality of sequentially ordered deployable medical appliances;
   a means, coupled to the at least one string, for affirmatively verifying that the specific medical appliance, from the plurality of medical appliances, has been deployed; and
   a stopper fixedly positioned on the outside surface of the body.

14. The apparatus of claim 13 wherein the body is polygonal.

15. An apparatus for selectively deploying one or more sequentially positioned medical appliances from a portable medical device to a target site, the apparatus comprising:
   a ligation tip having a plurality of sequentially ordered deployable medical appliances in contact with its outside surface,
      the ligation tip having an internal passage;
   a body having a channel, the channel in communication with the internal passage of the ligation tip;
   at least one string passing through the internal passage and the channel, the at least one string being associated with at least one of the medical appliances from the plurality of sequentially ordered deployable medical appliances;
   a means, coupled to the at least one string, for affirmatively verifying that the specific medical appliance, from the plurality of medical appliances, has been deployed; and
   an external sealing plug positioned along the outside surface of the body between the distal end and the proximal end, the external sealing plug having a passage sized to slidably couple the body to the external sealing plug.

16. The apparatus of claim 15 wherein the a means for affirmatively verifying that the specific medical appliance has been deployed is a plurality of pulls, each pull connected to an end of one of the at least one strings and having a unique marking to distinguish it.

* * * * *